United States Patent [19]

Chang

[11] Patent Number: 4,914,988
[45] Date of Patent: Apr. 10, 1990

[54] EYEBROW TATTOOING MACHINE

[76] Inventor: Meng-Cheng Chang, Rm. 10, 9th Fl., Sec. A, No. 255, Yen Ping N. Rd., Sec. 2, Taipei, Taiwan

[21] Appl. No.: 240,551

[22] Filed: Aug. 8, 1988

[51] Int. Cl.[4] .............................................. B43K 5/00
[52] U.S. Cl. ...................................... 81/9.22; 606/186
[58] Field of Search .......................... 81/9.22; 128/316

[56] References Cited

U.S. PATENT DOCUMENTS 4,204,438  5/1980  Binaris et al. ......................... 81/9.22
4,796,624  1/1989  Trott et al. ........................... 128/316

*Primary Examiner*—D. S. Meislin
*Attorney, Agent, or Firm*—Browdy and Neimark

[57] ABSTRACT

The present disclosure is concerned with an electrically rechargeable eyebrow tattooing machine which is particularly employed by female to do make-up on the eyebrow as a result of the lack of hair thereat. A small motor drives an eccentric cam which is further connected with a drive rod with an elongate needle detachably disposed at the front end thereof, and the motion of the eccentric cam produces a reciprocating movement on the elongate needle which is received in a casing with its pointy tip retractably sticking out of a small bore of a frontmost cap. The cap is provided with an opening on the wall so that cotton with dye liquid can be stuffed therein, and each time the needle can acquire small amount of dye liquid in its repeated motion through the dye contained cotton. The use of rechargeable source makes the operation of the present machine with less vibration and the small size facilitates the safe holding of the same in operation.

2 Claims, 4 Drawing Sheets

EYEBROW TATTOOING MACHINE

BACKGROUND OF THE INVENTION

For natural or social reason, make-up has been a primary concern for women of all ages and of different races for thousand of years. Eyebrow make-up is a major portion in a routine make-up, and particularly important for those women who have less or no hair at all on the eyebrows because of illness or age problems. To put make-up on the eyebrow by means of a general eyebrow pen is rather time consuming and requires great care not to mess it up; it has been widely practiced by women of all ages in the Chinese society to tattoo the eyebrow for quite a long history, thereby the task of make-up can be partially simplified.

Manual practice of the eyebrow tattooing has been replaced by way of using an automatic device having a fountain pen shaped front portion with a cylindrical tube rear portion attached thereto.

There are a number of inherent disadvantages associated with the prior eyebrow tattooing device, which are listed as below:

1. The use of an extension cord to couple the prior tattooing device to a power source makes the operation of the device unsafe because of the accidental pulling on the extension cord causing the tattooing device to move in an unexpected manner, hurting the user's eye easily.

2. The uneven distribution of the weight with its rear portion heavier than the front portion thereof, and the polished surface, makes the holding of the device difficult.

3. Most of the material used in the prior tattooing devices is metal, the processing on the device is not easy to perform, and the cost of production is relatively high.

4. The speed of operation is not variable; and the vibration of the prior tattooing device in operation makes the practice hard to perform.

5. Dye material used in the tattooing is put in a tray, and the needle of the prior tattooing device must be plunged in the dye material, making the needle wear out easily thus causing the tattooing to hurt thereby.

SUMMARY OF THE INVENTION

The primary object of the present invention is to provide an electrically operated eyebrow tattooing machine, the operation speed of which can be selected by the user. A small motor is used to drive an eccentric cam which actuates a drive rod with a needle removably attached thereon to vibrate in reciprocation in such a manner that no serious shaking is produced in operation, and the holding of the present machine becomes easy.

One other object of the present invention is to provide an electrically operated eyebrow tattooing machine which is of a compact size for easy and long-time holding by the user; and wherein the use of light weight plastic material makes production more economic and competitive.

One further object of the present invention is to provide an electrically operated eyebrow tattooing machine which is provided with a rechargeable battery; and the needle mounted thereon can be disposed of after use, so that the present machine is operated in a safer and more hygenic manner.

One still further object of the present invention is to provide an electrically operated eyebrow tattooing machine which is provided with a detachable cap at the front end thereof with an opening disposed thereon for the stuffing of cotton therein, and dye liquid is absorbed by the cotton so that the reciprocating needle can be provided with small amount of dye liquid in each motion to effect the tattooing of the eyebrow; and for different kinds of people, the color of the tattooing can be varied by replacing the cotton with a proper dye liquid containing therein.

DETAILED DESCRIPTION OF THE PREFERRED EMBODIMENT

Figure 1:
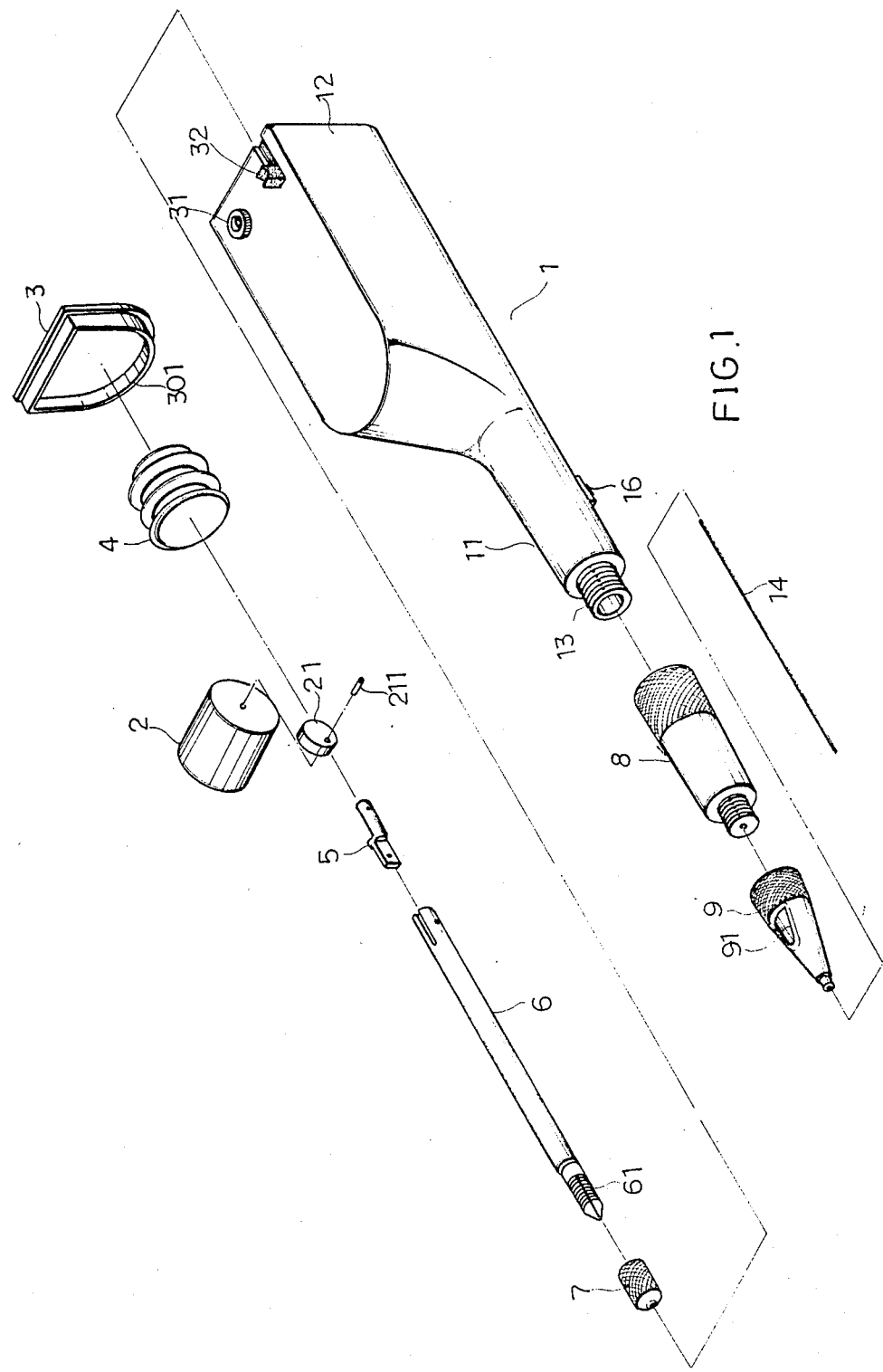
FIG. 1 is a diagram showing the exploded components of the present machine.
Figure 2:
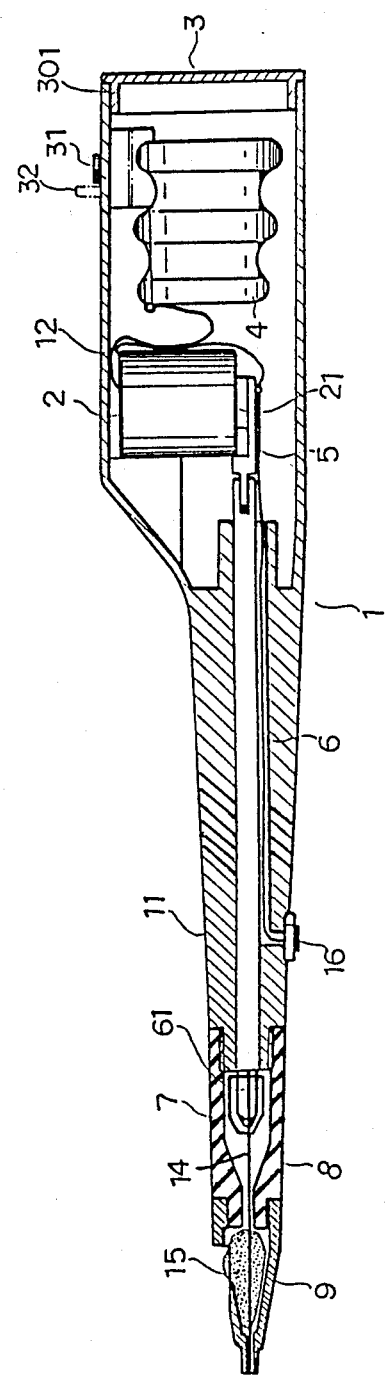
FIG. 2 is a longitudinal sectional view of the present invention.
Figure 3:
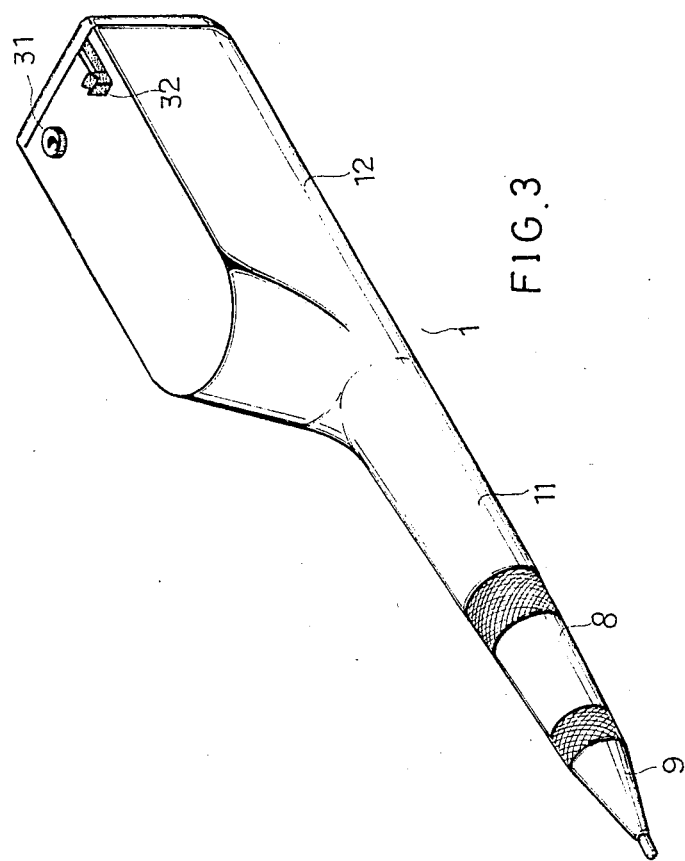
FIG. 3 is a perspective view of the present invention.
Figure 4:
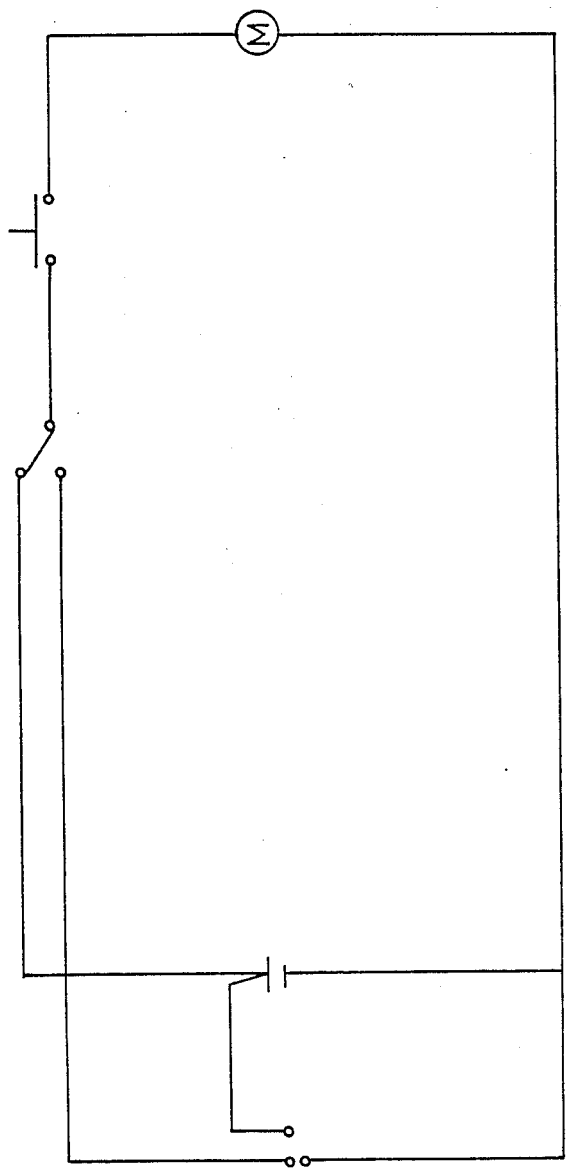
FIG. 4 is a diagram showing the circuit of the present invention.

Referring to FIGS. 1, 2, the present eyebrow tattooing machine comprises a casing 1, a motor 2, a cover 3, a rechargeable battery 4, a connecting member 5, a drive rod 6, a fixing head 7, a first cap 9 and a second cap 8. The casing 1 consists of an extended tube member 11 and a hollow interior member 12 that are integrally formed as a unit.

The motor 2 and rechargeable battery 4 are housed in the hollow interior member 12. The output shaft of the motor 2 is connected with an eccentic cam 21, the shaft pin 211 of which is coupled to one end of the connecting member 5. The other end of the connecting member 5 is engaged with the drive rod 6. The drive rod 6 is received the tube member 11 of the casing 1. The front end of the drive rod 6 is provided with a clamping claw 61. A fixing head 7 is engaged by threads with the clamping claw 61.

A threaded end 13 is projected from the front end of the tube member 11 and is engaged first with a second cap 8 which is then engaged with a first cap 9, also by way of threaded ends. The cone-shaped first cap 9 is furnished with a triangular opening 91 on the periphery, near the middle section thereof.

An elongate needle 14 is firmly held at one end by the clamping claw 61 of the drive rod 6 in cooperation with a fixing head 7. The needle 14 is housed within the interior of the assembled first cap 9 and second cap 8. Cotton 15 can be stuffed into the triangular opening 91 of the first cap 9 so that dye liquids of various colors can be selectively used for various hair colors of different people.

The hollow interior member 12 of the casing 1 is equipped with a cover 3 which has a peripheral flange 301 disposed at one side thereof so that it can be firmly engaged with the opening at the rear end of the casing 1. On the top wall of the casing 1 are disposed an on/off switch 32, and a plug inlet 31 which is for the insertion of an electric source for charging purpose. A motor-control button 16 is provided on the underside of the tube member 11 for the controlling the starting and stopping of the motor.

Before use, the rechargeable battery 4 is first charged with electricity, then pushing the motor-control button 16 will actuate the motor 2 and leads to the motion of the eccentric cam 21. At the same time the drive rod 6 will move in reciprocation as the result of the connection by the connecting member 5 with the eccentric cam 21. Therefore the elongate needle 14 with its end engaged with the drive rod 6 will reciprocatingly move with the front tip thereof retractably extending out of the frontmost bore of the first cap 9. The dye liquid absorbed in the cotton 15 will be delivered along with the tip of the needle so that the eyebrow of the operator can be tattooed with the dye liquid penetrating the superficial skin of the person using the machine.

The power to operate the present machine may come either from a DC or an AC electrical source. When power is from an AC source, a rectifier is adopted. Moreover, the needle 14 is disposable after use, and a brand new needle is mounted for next operation, thereby a more hygenic way is effected. The use of the rechargeable battery facilitates the operation of the machine, making the operator free from the restraint of the power cord, and the vibration of the machine is also effectively reduced to a satisfactory extent.

What I claim is:

1. An electrically operated eyebrow tattooing machine, comprising:
   a casing;
   a small motor having an output shaft;
   a rear cover detachably engaged with said casing;
   a connecting member having a first and second end;
   a drive rod having a first end engaged with the first end of said connecting member;
   a fixing head detachably engaged by threads with a front end of said drive rod;
   a first cap of cone shape having a small bore at a front end and a threaded portion at a second end;
   a second cap having an extended threaded end for the engagement of the same to the threaded portion of said first cap; and
   an elongate needle;
   a rechargeable battery;
   an eccentric cam having a shaft pin engaged with the second end of said connecting member;
   a plug inlet;
   a motor-control button for controlling the start and stop of said small motor;
   wherein said casing includes a hollow interior member and an extended tube member integrally structured with said hollow interior member, said tube member having a threaded end having a smaller diameter than said tube member so that said second cap can be engaged therewith; said small motor and said rechargeable battery are housed within said hollow interior member; on the top wall of said casing are disposed an on/off switch and said plug inlet for use in electrical charge of said rechargeable battery; said drive rod is disposed within said extended tube member; and said eccentric cam is mounted on the output shaft of said small motor; a second end of said drive rod is provided with a clamping claw, and said fixing head is in cooperation with said clamping claw to hold said elongate needle in place which is partially inserted in said clamping claw; the first cap and second cap are adapted to be connected to each other as one unit and further joined with the casing, and the needle held in place by said drive rod actuated to move in reciprocation by said eccentric cam is received in the interior of said first and second cap and said tube member; said conical first cap is stuffed with cotton material therein so that a dye substance can be contained therein; said needle is adapted to selectively extend out of the small bore of said first cap so that tattooing on the eyebrow can be performed by the tip of the elongate needle.

2. An electrically operated eyebrow tattooing machine as claimed in claim 1 wherein the conical first cap is provided with an opening on the wall thereof so that the dye substance can be directly fed into the first cap and absorbed by the cotton for tattooing use.

* * * * *